United States Patent
Wang et al.

(10) Patent No.: US 9,006,568 B2
(45) Date of Patent: Apr. 14, 2015

(54) SYNTHESIS OF PHOTOVOLTAIC CONJUGATED POLYMERS

(71) Applicants: Phillips 66 Company, Houston, TX (US); Solarmer Energy, Inc., El Monte, CA (US)

(72) Inventors: Shuangxi Wang, El Monte, CA (US); Chenjun Shi, El Monte, CA (US); Ruby Chen, El Monte, CA (US); Junlian Zhang, El Monte, CA (US); Hui Huang, Bartlesville, OK (US); Yue Wu, El Monte, CA (US); Wei Wang, El Monte, CA (US); Amit Palkar, Bartlesville, OK (US); Ting He, Bartlesville, OK (US)

(73) Assignees: Phillips 66 Company, Houston, TX (US); Solarmer Energy, Inc., El Monte, CA (US)

(*) Notice: Subject to any disclaimer, the term of this patent is extended or adjusted under 35 U.S.C. 154(b) by 171 days.

(21) Appl. No.: 13/764,919

(22) Filed: Feb. 12, 2013

(65) Prior Publication Data
US 2013/0214213 A1    Aug. 22, 2013

Related U.S. Application Data

(60) Provisional application No. 61/599,419, filed on Feb. 15, 2012.

(51) Int. Cl.
C07D 333/02    (2006.01)
C07D 333/04    (2006.01)
(Continued)

(52) U.S. Cl.
CPC .......... *H01L 51/0036* (2013.01); *C07D 409/02* (2013.01); *H01L 51/0037* (2013.01);
(Continued)

(58) Field of Classification Search
CPC .... Y02E 10/50; Y02E 10/549; C07D 333/02; C07D 333/04; C07D 409/02
USPC .................................. 136/263; 549/29, 32, 70
See application file for complete search history.

(56) References Cited

U.S. PATENT DOCUMENTS

| 7,928,237 B2 * | 4/2011 | Clark et al. ...................... 546/83 |
| 2005/0176684 A1 * | 8/2005 | Bookser et al. .................. 514/86 |

(Continued)

FOREIGN PATENT DOCUMENTS

| EP | 1279690 A1 | 1/2003 |
| WO | WO-03032072 A2 | 4/2003 |

(Continued)

OTHER PUBLICATIONS

Kleinhenz et al., *Low-band-gap polymers that utilize quinoid resonance structure stabilization by thienothiophene: Fine-tuing of HOMO level*, Macromolecules 44(4) (2011) 872-877.

(Continued)

*Primary Examiner* — Gregory R Delcotto
(74) *Attorney, Agent, or Firm* — Garder Wynne Sewell LLP; Chris P. Perque; Teresa J. Lechner-Fish

(57) ABSTRACT

A method of making a fluorothieno[3,4-b]thiophene derivatives and photovoltaic polymers containing same using 3-bromothiophene-2-carboxylic acid as a starting material. This synthetic route provides an easier synthesis as well as greater yield and a purer product, which produces superior results over the prior art less pure products. The resulting materials can be used in a variety of photovoltaic applications and devices, especially solar cells.

4 Claims, 5 Drawing Sheets

(51) Int. Cl.
*C07D 409/02* (2006.01)
*H01L 51/00* (2006.01)
*C07D 495/04* (2006.01)
*C08G 61/12* (2006.01)
*H01L 51/42* (2006.01)

(52) U.S. Cl.
CPC ....... H01L51/4253 (2013.01); H01L 2251/308 (2013.01); *C07D 495/04* (2013.01); *C08G 61/126* (2013.01); C08G 2261/124 (2013.01); C08G 2261/1412 (2013.01); C08G 2261/1426 (2013.01); C08G 2261/1428 (2013.01); C08G 2261/146 (2013.01); C08G 2261/149 (2013.01); C08G 2261/3243 (2013.01); C08G 2261/91 (2013.01); Y02E 10/549 (2013.01)

(56) References Cited

U.S. PATENT DOCUMENTS

| | | | |
|---|---|---|---|
| 2006/0071200 | A1 | 4/2006 | Nordquist et al. |
| 2006/0223977 | A1 | 10/2006 | Zahn et al. |
| 2009/0159120 | A1 | 6/2009 | Wang et al. |
| 2009/0159131 | A1 | 6/2009 | Zheng et al. |
| 2009/0159999 | A1 | 6/2009 | Zheng et al. |
| 2010/0006148 | A1 | 1/2010 | Zheng et al. |
| 2010/0018581 | A1 | 1/2010 | Shrotriya et al. |
| 2010/0078074 | A1 | 4/2010 | Yang et al. |
| 2010/0101636 | A1 | 4/2010 | Zheng et al. |
| 2010/0224832 | A1 | 9/2010 | Jou et al. |
| 2010/0276071 | A1 | 11/2010 | Shrotriya et al. |
| 2010/0300520 | A1 | 12/2010 | Su et al. |
| 2010/0326497 | A1 | 12/2010 | Yang et al. |
| 2011/0008926 | A1 | 1/2011 | Irvin et al. |
| 2011/0031875 | A1 | 2/2011 | Jou et al. |
| 2011/0086994 | A1* | 4/2011 | Wigglesworth et al. ...... 526/256 |
| 2011/0124822 | A1* | 5/2011 | Yu et al. ............ 525/389 |
| 2011/0147725 | A1 | 6/2011 | Seshadri |
| 2012/0071617 | A1 | 3/2012 | Dueggeli et al. |
| 2012/0118368 | A1 | 5/2012 | Huang et al. |
| 2012/0232237 | A1 | 9/2012 | Li et al. |
| 2012/0264906 | A1 | 10/2012 | Marks et al. |

FOREIGN PATENT DOCUMENTS

| | | |
|---|---|---|
| WO | WO-2010008672 A1 | 1/2010 |
| WO | WO-2011111545 A1 | 9/2011 |
| WO | WO-2012074853 A1 | 6/2012 |
| WO | WO-2012142460 A1 | 10/2012 |
| WO | WO-2012142469 A1 | 10/2012 |

OTHER PUBLICATIONS

PCT May 7, 2014 International Search Report and Written Opinion issued in International Patent Application PCT/US13/70674.

Chen, Hsiang-Yu, et al., *Polymer solar cells with enhanced open-circuit voltage and efficiency*, Nature Photonics, 2009, 3, pp. 649-653.

Huo, Linjun, et al., *Replacing alkoxy groups with alkylthienyl groups: A feasible approach to improve the properties of photovoltaic polymers*, Angew. Chem. Int. Ed., 2011, 50(41), pp. 9697-9702.

Liang, Yongye, et al., *Development of new semiconducting polymers for high performance solar cells*, J. Am. Chem. Soc., 2009, 131(1), pp. 56-57.

Liang, Yongye, et al., *For the bright future—Bulk heterojunction polymer solar cells with power conversion efficiency of 7.4%*, Adv. Mater., 2010, (22), pp. E135-E138.

Liang, Yongye, et al., *Highly efficient solar cell polymers developed via fine-tuning of structural and electronic properties*, J. Am. Chem. Soc., 2009, 131(22), pp. 7792-7799.

International Search Report issued Apr. 30, 2013 for International Application PCT/US2013/026092.

US 8,022,391, 09/2011, Sargent et al. (withdrawn)

* cited by examiner

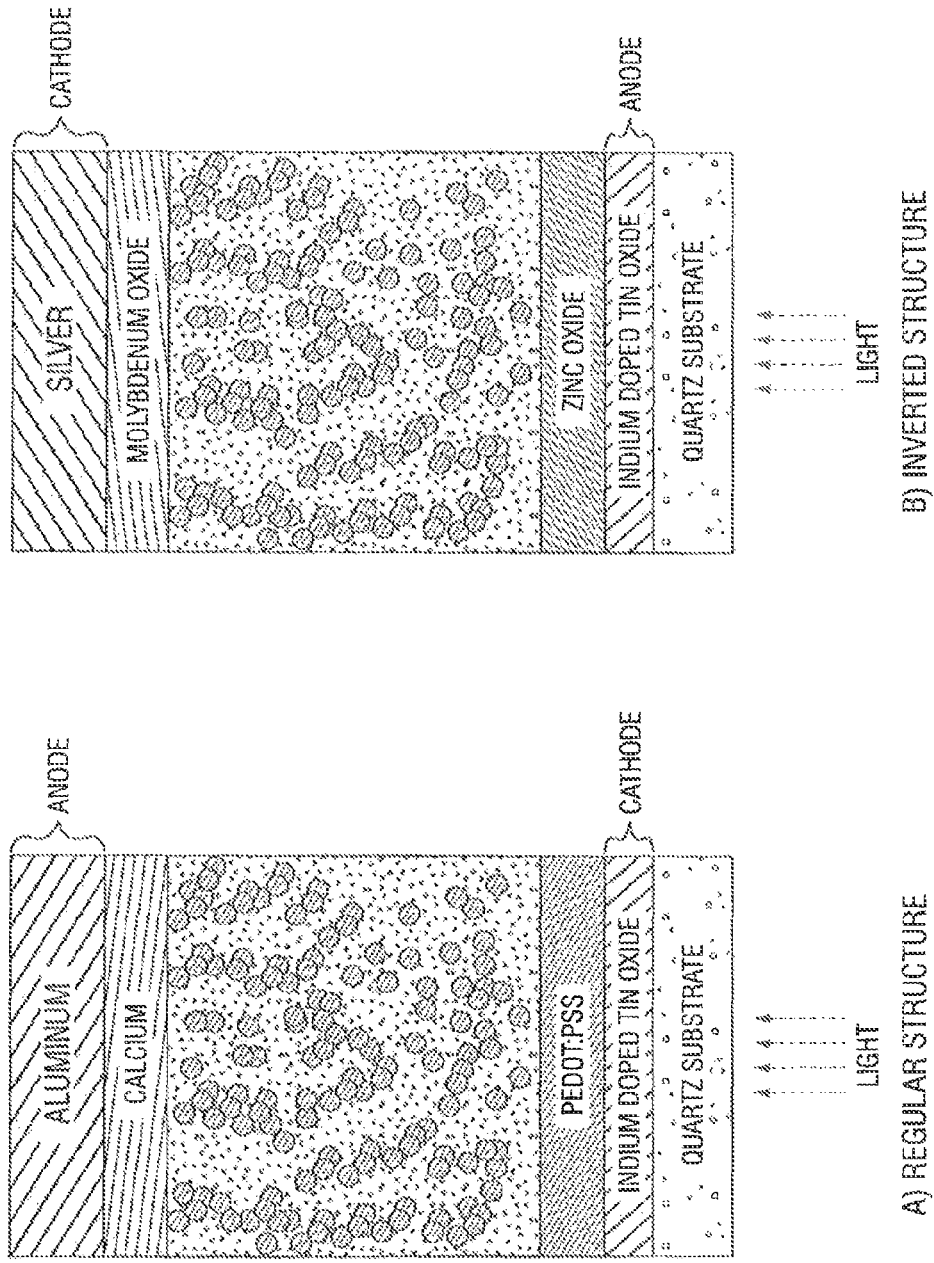
FIG. 7A  A) REGULAR STRUCTURE
FIG. 7B  B) INVERTED STRUCTURE ively efficient. This is a major advantage of inorganic solar cells over organic devices, which have less than a third of the efficiency of silicon-based cells. However, inorganic solar cells also possess disadvantages. Their production is costly and energy consuming because it requires a thorough purification procedure, and the environmental impact of their synthesis and use is high. Therefore, inorganic cells still cannot provide cost-efficient alternative to other 'green' energy sources, such as hydropower.
SYNTHESIS OF PHOTOVOLTAIC CONJUGATED POLYMERS

PRIOR RELATED APPLICATIONS

This application claims the benefit of U.S. Provisional Application Ser. No. 61/599,419 for "Synthesis of Photovoltaic Conjugated Polymers," filed on Feb. 15, 2012.

FEDERALLY SPONSORED RESEARCH STATEMENT

Not Applicable ("N/A")

REFERENCE TO MICROFICHE APPENDIX

N/A

FIELD OF INVENTION

The invention relates to a method for making conjugated polymers for organic photovoltaic applications, and, in particular, to a method for making high performance conjugated polymers with a high conversion rate and where the product can be easily purified from unreacted reactants.

BACKGROUND OF THE INVENTION

The term "photovoltaic" comes from the Greek phos meaning "light", and "voltaic", from the name of the Italian physicist Volta, after whom the unit of electro-motive force—the volt—is named. Photovoltaics are, therefore, related to the practical application of photovoltaic cells to produce electricity from light, even though the term is often used specifically to refer to the generation of electricity from sunlight.

Harvesting solar energy using the photovoltaic effect requires active semiconducting materials to convert light into electricity. Currently, solar cells based on silicon are the dominant technology due to their high conversion efficiency. Mono-layered inorganic solar cells are composed of an inorganic semiconductor sandwiched between two metallic electrodes with different electrochemical potentials (Fermi levels), where one of electrodes is semi-transparent or grid-like. They generate voltage when light penetrates into the semiconductor. A photon breaks a covalent bond between silicon atoms and 'kicks' one electron out. The atom that loses the electron gets a positive charge and becomes a hole. Further electrons are transported to the anode and holes to the cathode driven by a difference in electrochemical potentials of the electrodes. Mono-layered devices usually possess low power conversion efficiency.

Bi-layered devices are composed of two types of semiconductor: p-type and n-type. In this case, the charge separation occurs near the border between p-type and n-type semiconductors and it is much more efficient, because the charges are 'captured' and held strong by 'host' semiconductors. Triple-layered and multi-layered devices are also known.

Inorganic solar cells are chemically and thermally stable devices, and power conversion efficiencies of modern inorganic solar cells reach the 30% barrier, and therefore they are relatively efficient. This is a major advantage of inorganic solar cells over organic devices, which have less than a third of the efficiency of silicon-based cells. However, inorganic solar cells also possess disadvantages. Their production is costly and energy consuming because it requires a thorough purification procedure, and the environmental impact of their synthesis and use is high. Therefore, inorganic cells still cannot provide cost-efficient alternative to other 'green' energy sources, such as hydropower.

Recently, solar cells based on organic materials have been developed, although to date they are far less efficient than silicon based cells. Advantages of organic solar cells are that they are lightweight and more environmentally friendly. There is no need for rare metals and minerals, and no need for high temperatures and purity at the production stage. Thus, inorganic solar cells are potentially very inexpensive to make and there is virtually unlimited room for further material modification and improvement.

Operation of organic solar cells is mechanistically more complex than that of inorganic solar cells. First, a molecule of an organic compound absorbs a photon and forms an excited state (exciton). Further, the exciton diffuses to a junction border between n- and p-types of semiconductor where it dissociates to form free charge carriers. Organic p- and n-transporters are also known as donors and acceptors correspondingly. If there is no junction border nearby, the exciton may recombine (decay) via photoluminescence, or thermally, back into the ground state of the molecule. This non-productive decay pathway is the main reason that mono- and bilayered organic solar cells were poorly performing devices, until the new concept of bulk heterojunction cells was introduced.

An organic bulk heterojunction cell consists of two electrodes (anode and the cathode) which sandwich the photoactive layer of a device (see FIG. 1). A bulk heterojunction is a tight blend of a p-type conductor (donor), and n-type conductor (acceptor) in the photoactive layer of a device, where the concentration of each component often gradually increases when approaching the corresponding electrode. This affords vast expansion of p-n-junction's total surface and strongly facilitates the exciton's dissociation into positive (holes) and negative (electrons) charges. The anode and the cathode collect the electrons and the holes respectively. The anode is usually coated with an electron transport layer to facilitate the movement of electrons to this electrode. Similarly, the cathode is maybe coated with a hole transport layer which facilitates the collection of positive charges (holes). The implication of this concept in practice allows increase of power conversion efficiencies of up to 5% for all-organic solar cells. The entire device is encapsulated using a suitable material to prevent leakage of moisture and oxygen.

In spite of the impressive results achieved with the realization of the bulk-heterojunction concept, the organic cells and materials still need to be strongly improved in order to find commercial application. Current organic solar cells exhibit low power conversion efficiency, about 4%-5%, compared with silicon based solar cells, even after sophisticated device optimization. In fact, the best efficiency achieved to date has been about 8% efficiency, but these are lab-based results only and, therefore, are not generally achievable, and there is always room for further improvement.

Conjugated polymers have shown some promise in providing a photovoltaic effect. Conjugated polymers are made of alternating single and double carbon-carbon (C—C) or carbon-nitrogen (C—N) bonds. The conjugated polymers have a δ-bond backbone of interesting $sp^2$ hybrid orbitals. The $p_z$ orbitals on the carbon atoms overlap with neighboring $p_z$ orbitals to provide π-bonds. The electrons that comprise the π-bonds are delocalized over the whole molecule. These polymers exhibit electronic properties similar to those seen in inorganic semiconductors. The semiconducting properties of the photovoltaic polymers are derived from their delocalized π-bonds.

WO03032072, as an example, describes a number of highly conjugated polymers that exhibit photovoltaic effects. Some of those compounds include thieno[3,4-b]thiophene related compounds, including octyl-6-dibromo-3-fluorothieno[3,4-b]thiophene-2-carboxylate. Thieno[3,4-b]thiophene derivatives, such as TT and FTT, are conjugated molecules that show a photoelectric effect and have the following chemical structures:

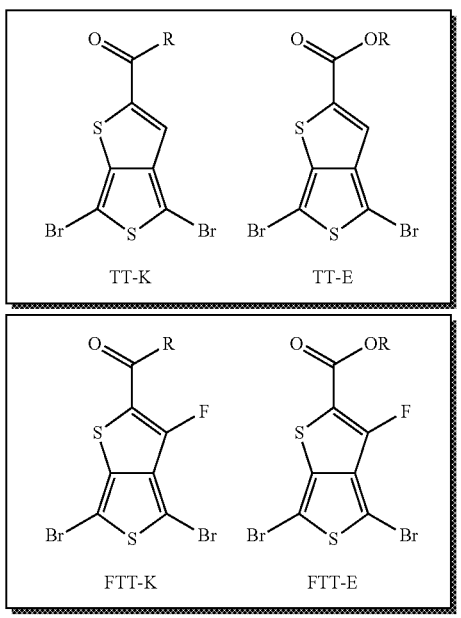

R = alkyl or aryl groups

Yongye Liang, et al., *Development of New Semiconducting Polymers for High Performance Solar Cells*, J. AM. CHEM. SOC. 131 (2009a) pp. 56-57, for example, describes a highly processible and stable semiconducting polymer called PTB 1, based on alternating thieno-[3,4-b]thiophene and benzodithiophene monomers. Simple solar cells prepared from the blend of this polymer and fullerene derivatives exhibit a high solar energy conversion efficiency of 5.6% and high fill factor of over 65%.

Yongye Liang, et al., *Highly Efficient Solar Cell Polymers Developed via Fine-Tuning of Structural and Electronic Properties*, J. AM. CHEM. SOC. 131 (2009b) pp. 7792-7799 developed further variations of the above polymer, as follows:

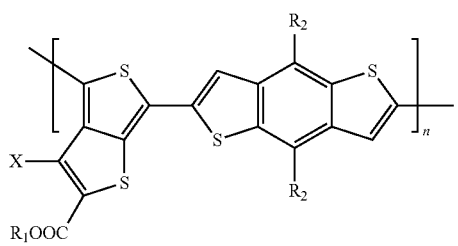

PTB1: X = H, $R_1$ = n-dodecyl, $R_2$ = n-octyloxy
PTB2: X = H, $R_1$ = 2-ethylhexyl, $R_2$ = n-octyloxy
PTB3: X = H, $R_1$ = 2-ethylhexyl, $R_2$ = n-octyl
PTB4: X = F, $R_1$ = n-octyl, $R_2$ = 2-ethylhexyloxy;
PTB5: X = H, $R_1$ = n-octyl, $R_2$ = 2-ethylhexyloxy
PTB6: X = H, $R_1$ = 2-butyloctyl, $R_2$ = n-octyloxy These polymers were mixed with $PC_{61}BM$ or $PC_{71}BM$ and simple solar cells were made and evaluated. The HOMO energy levels of the polymer were lowered by substituting alkoxy side chains to the less electron-donating alkyl chains in PTB3 or introducing electron-withdrawing fluorine into the polymer backbone in PTB4, leading to significant increase in VOC (28%) for polymer solar cells. The side chains and substitute groups also affect the polymer's absorption and hole mobility, as well as the miscibility with fulleride, all influencing polymer solar cell performances. Films prepared from mixed solvent exhibit finely distributed polymer/fulleride interpenetrating network and show significantly enhanced solar cell conversion efficiency.

A power conversion efficiency of over 6% was achieved in solar cells based on fluorinated $PTB4/PC_{61}BM$ composite films prepared from mixed solvents. However, the synthesis of the fluorinated monomer was substantially less than satisfactory. The fluorine was introduced to the fused ring unit from 4,6-dihydrothieno[3,4-b]thiophene-2-carboxylic acid after deprotonation by using BuLi and reacting with $PhSO_2NF$. However, this reaction produced only a mixture containing fluorinated product and unfluorinated reactant with a 4:1 ratio and a yield of only 65%, and which still needed to undergo further reaction to yield the dibrominated monomer at an overall yield of about 25%. See also US20110124822 and WO2010008672. Thus, it is expected that the 6% PCE may be improved if the synthesis could be improved and the resulting product would be more pure.

Later in WO2010008672, also by the Yongye Liang group, the benzo[1,2-b:4,5-b']dithiophene-fluorothienothiophene (BDT-FTT aka LY-16 therein) (see below) was shown to have reached 6.1% conversion efficiency in bulk-heterojunction (BHJ) solar cells. The improved performance was achieved by using mixed solvents in preparing polymer/fullerides spin-coating solution, which resulted in a more even morphology. Thus, the BDT-FTT/$PC_{61}$BM blend film exhibited improved morphology by using dichlorobenzene/1,8-diiodooctane (97/3, v/v) as solvent. There were no large features in the TEM image of a film layer using this method.

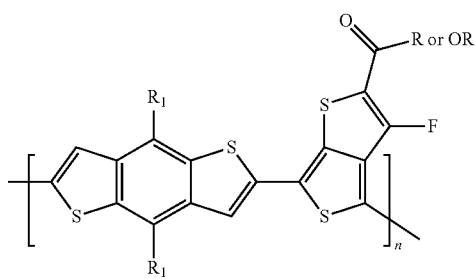

However, as already noted, conventional methods for synthesizing BDT-FTT suffer several drawbacks. First, it is difficult to isolate the fluorinated product from non-fluorinated starting materials. Further, the overall yield of the conventional synthetic method is less than 20%, meaning the manufacturing of BDT-FTT is not economically efficient. Further, the quality of the product is less than desired, negatively affecting cell efficiency.

Therefore, there is the need for a method for synthesizing BDT-FTT with high yield and wherein one can easily isolate the product from unreacted starting materials.

SUMMARY OF THE INVENTION

The present invention provides a synthetic method for synthesizing FTT and its derivatives, copolymers made with same, and BDT-FTT and related polymers with high conversion rate and purity.

As a general matter, using 3-bromothiophene-2-carboxylic acid or a protected derivative thereof as the starting material is crucial to this novel synthetic route. The synthetic method of the present invention can achieve high conversion rates, especially in the crucial step of converting the brominated intermediate to fluorinated intermediate. The conversion rate is significantly improved from less than about 20% seen in the prior art to about 60-80% conversion. Further, the final product has less than about 10% of the unfluorinated compound, preferably less than about 7%, about 5%, about 2%, or about 1%, whereas the prior art method had at least 20% of the unfluorinated reagent.

In one embodiment, the invention is a method of making a fused heterocycle, comprising using a compound according to formula (I) or a protected derivative thereof as a starting material:

(I)

to form a fused heterocycle of formulae (II) or (III):

(II)

(III)

wherein R is hydrogen, $C_1$-$C_{20}$ alkyl, $C_1$-$C_{20}$ haloalkyl, aryl, heteroaryl, $C_1$-$C_{20}$ alkoxy, $C_1$-$C_{20}$ haloalkoxy, aryloxy, —$C_1$-$C_{20}$ alkyl-O—$C_1$-$C_{10}$ alkyl, —$C_1$-$C_{10}$ alkyl-O-aryl, nitro, halo, amino, or mono- or di alkyl amino.

In another embodiment, the method includes the following reactions: i) protection of carboxylic acid with a protection group, ii) chloromethylation with two chloromethyl groups, iii) a cyclization reaction at the two chloromethyl groups, iv) hydrolysis of the carboxylate protection group, v) exchange fluorine for bromine, and vi) optional esterification of the carboxylate.

The method can include the following steps or their equivalents:

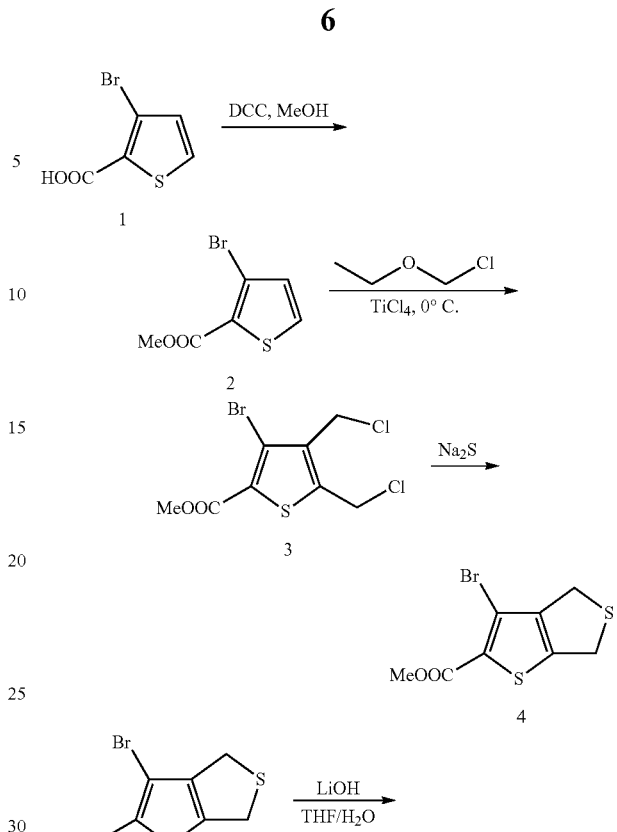

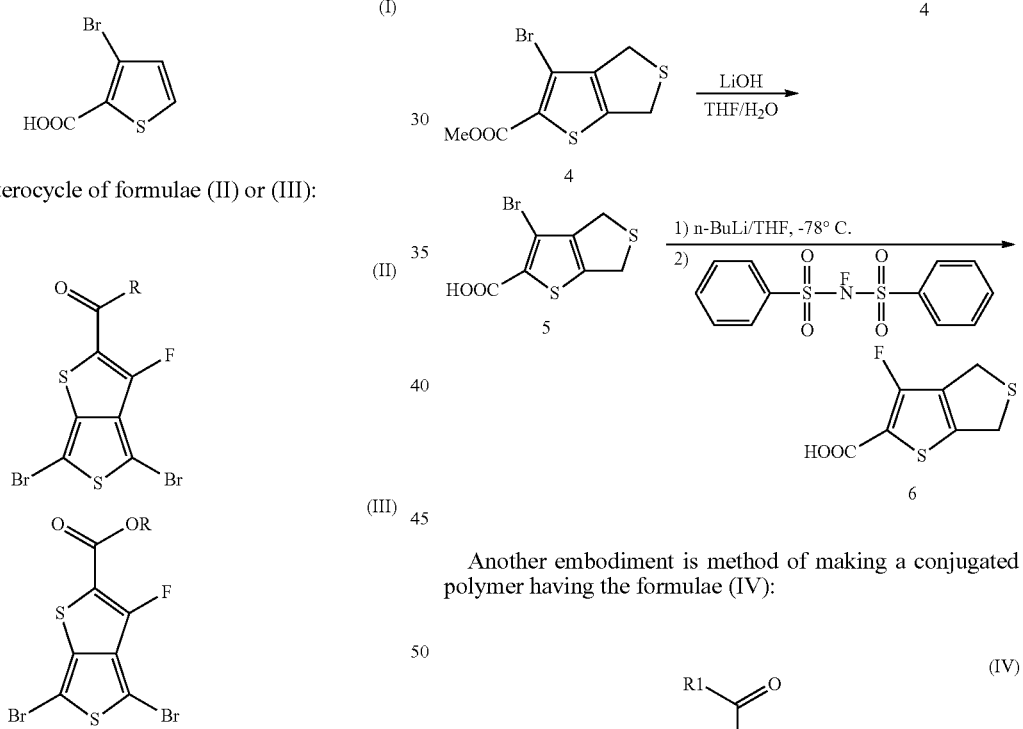

Another embodiment is method of making a conjugated polymer having the formulae (IV):

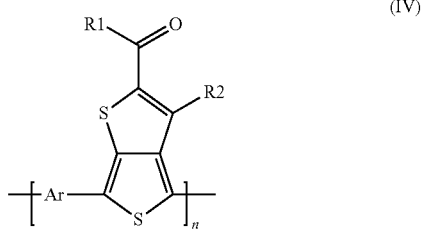

(IV)

wherein R1 is proton, halogens, alkyls, —O-alkyls, substituted alkyls, amino, N-substituted amino groups, aryls and substituted aryls; Ar is selected from the group consisting of ethenylene, or ethynylene, or monocyclic, bicyclic and polycyclic arylenes, or monocyclic, bicyclic and polycyclic heteroarylenes, or unit being comprised of two or more compounds choosing from ethenylene, ethynylene, or monocyclic, bicyclic and polycyclic arylene, or monocyclic, bicyclic and polycyclic heteroarylenes; wherein R2 is F; and wherein said conjugated polymer is made using compound according to formula (I) or a protected derivative thereof as a starting material.

In another embodiment, the conjugated polymer is of formulae (V):

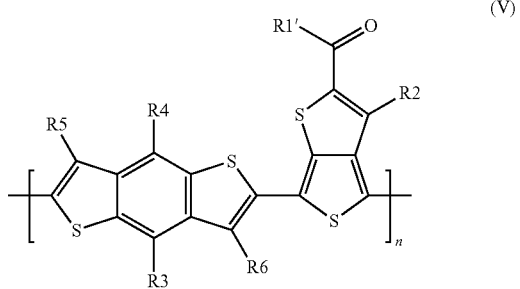

wherein R1' is selected from proton, alkyls, substituted alkyls, aryls, substituted aryls; wherein R2 is F; and wherein R3, R4, R5 and R6 are selected independently from proton, alkyls, substituted alkyls, alkoxyls, substituted alkoxyls, halogens, aryls, substituted aryls.

In another embodiment, the conjugated polymer is of formulae (VI):

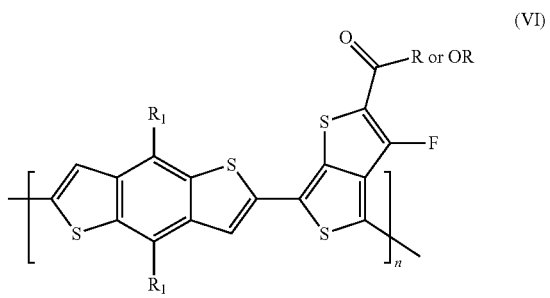

wherein R and R1 are independently selected from proton, halogens, alkyls, substituted alkyls, amino, N-substituted amino groups, aryls and substituted aryls.

The invention also includes photovoltaic device comprising the polymer made herein on a substrate, as well as solar cells.

The FTT and derivatives synthesized herein can be used to make any photovoltaic polymers known or to be developed in the art. A particularly preferred photovoltaic polymer is BDT-FTT and various derivatives thereof.

We have made an exemplary photovoltaic device using the BDT-FTT made herein, and found it to perform better than a device using BDT-FTT made by prior art methods, proving that the synthetic method produces high quality polymer having superior performance in BHJ solar cells.

The conjugated polymers as synthesized herein can be used in any application for which they are suitable, including use in organic solar cells and other photoelectric applications. Another aspect of the present invention includes the use of the FTT-based polymers and copolymers made as described herein in devices such as a solar cell, an optical device, an electroluminescent device, a photovoltaic cell, semiconducting cell, photodiode, polymeric field effect transistors.

Solar cells can be of any design known or to be developed including those described in US20110008926, which describes conductive material grids or lines embedded or partially embedded in a transparent substrate of a solar cell, and US20100276071 and US20100326497, which describe tandem solar cells, and US20100018581, which describes large area solar cells wherein the anode is larger than the cathode. Other solar cell designs include simple bulk heterojunction photovoltaic cells, graded heterojunction photovoltaic cells, folded or ordered bulk heterojunction photovoltaic cells, double-layer p-n junction photovoltaic cells, and inverted bulk heterojunction photovoltaic cells The photoactive polymers described herein can be joined with electron accepting materials including, but not limited to, Buckminsterfullerene ("fullerene") derivatives, or other doping materials in order to fine-tune their properties. Any electron accepting fullerene can be used with the semiconducting polymers described herein. Such fullerenes can be from $C_{60}$ to $C_{90}$. In preferred embodiments the fullerene can be $C_{61}$, $C_{71}$, $C_{81}$, or $C_{91}$. Preferred fullerenes are [6,6]-phenyl-$C_{61}$-butyric acid methyl ester ($PC_{61}BM$) or the $C_{71}$ variant (PC71BM). The polymer and fullerene can blend as a mixture. Suitable dopants can include Leuco Crystal Violet (LCV), zinc phthalocyanine (ZnPc), gold, copper, palladium, and iodine.

A method of incorporating the semiconducting polymers described herein onto a substrate comprises dissolving one or more of the polymers described herein with a fullerene derivative and/or dopant in a solvent or mixed solvent and applying the resulting composite blend onto a substrate. Preferred mixed solvents include dichlorobenzene/1,8-di-iodooctane (97/3, v/v) or di-chloromethane and hexane mixed solvents, and the like.

Methods of coating substrates include spin coating, vapor phase deposition, vacuum thermal evaporation, organic vapor phase deposition, and the like. Other methods can include nano-imprint lithography and other inkjet-like printing methods.

Suitable substrates, such as Indium Tin Oxide (ITO)-coated glass or flexible substrates such as poly(ethylene terephthalate)-foil (PET), poly(ethylene naphthalate)-(PEN) and poly(imide)-foil (PI), are known in the art and can be used.

Thus, a thin-film solar cell (TFSC), also called a thin-film photovoltaic cell (TFPV), is a solar cell that is made by depositing one or more thin layers (thin film) of photovoltaic material on a substrate, and thickness range of such a layer is wide and varies from a few nanometers to tens of micrometers. The layer of composite blend is preferably from about 80 nm to about 150 nm thick, but layer thickness will vary depending on the application.

As used herein, "starting material" means that the recited chemical is made or purchased for use as an early reactant in the synthetic pathway. However, if made, rather than purchased, there may be other ingredients that pre-date same. Nonetheless, using 3-bromothiophene-2-carboxylic acid is to be recognized as a starting material for FTT and its derivatives, as well as for BDT-FTT and its derivatives because it is used on an early starting material in the synthetic pathway.

These and other objects, features, and advantages will become apparent as reference is made to the following detailed description, preferred embodiments, and examples, given for the purpose of disclosure, and taken in conjunction with the accompanying drawings and appended claims.

BRIEF DESCRIPTION OF THE DRAWINGS

For a further understanding of the nature and objects of the present inventions, reference should be made to the following detailed disclosure, taken in conjunction with the accompanying drawings, in which like parts are given like reference numerals, and wherein:

FIG. 7a shows the test photovoltaic device of Example 5A; and

FIG. 7b shows the test photovoltaic device of Example 5B.

DETAILED DESCRIPTION OF EMBODIMENTS OF THE INVENTION

The following detailed description of various embodiments of the present invention references the accompanying drawings, which illustrate specific embodiments in which the invention can be practiced. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. Therefore, the scope of the present invention is defined only by the appended claims, along with the full scope of equivalents to which such claims are entitled.

The invention provides a novel method for synthesizing FTT derivatives with high yield and easy to purify product. Specifically, 3-bromothiophene-2-carboxylic acid is used as a starting material instead of thiophene-2-carboxylic acid, so as to have improved fluorination conversion rate.

EXAMPLE 1

Synthesis of FTT-K

Figure 1:
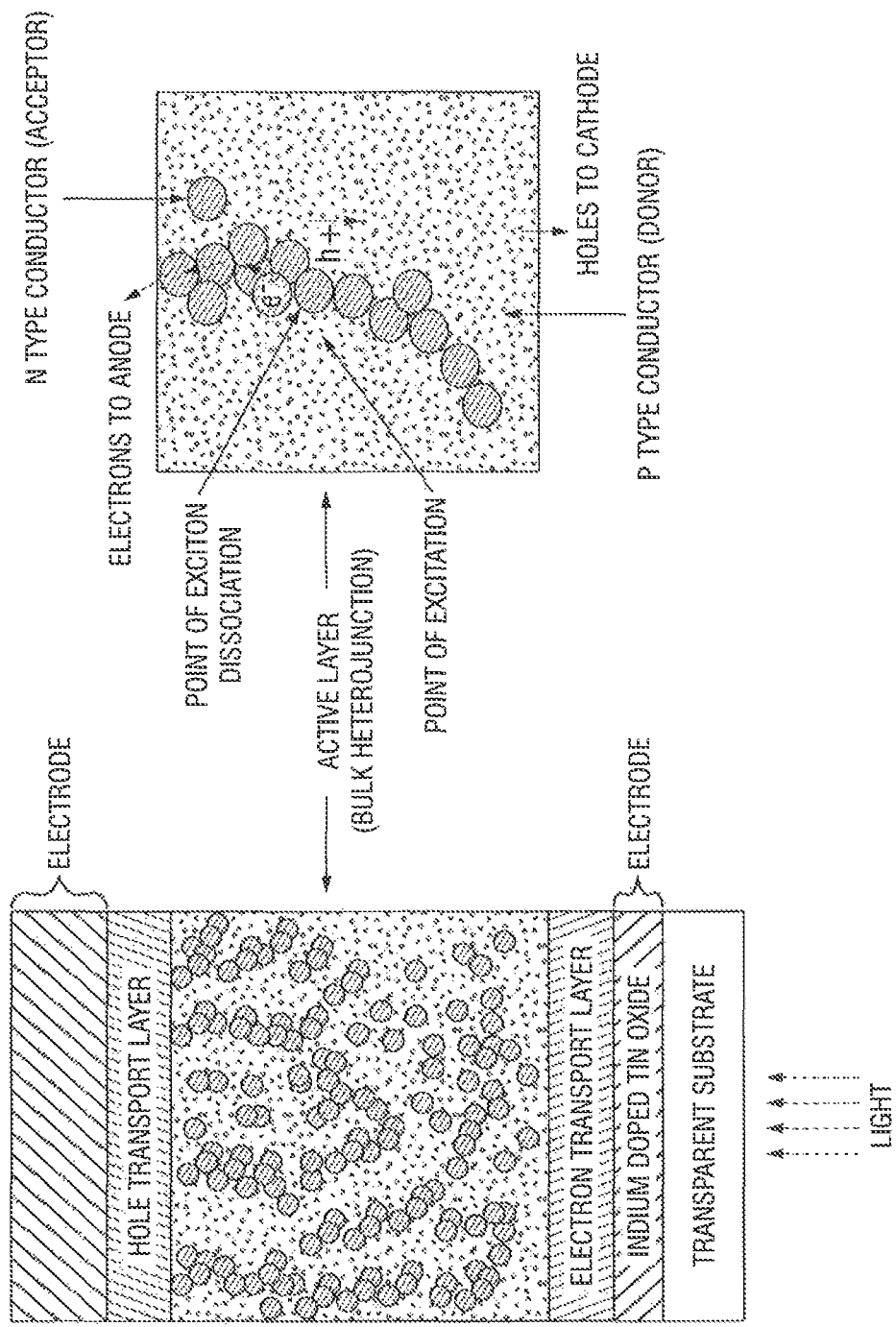
FIG. 1 shows a bulk heterojunction.
Figure 2:
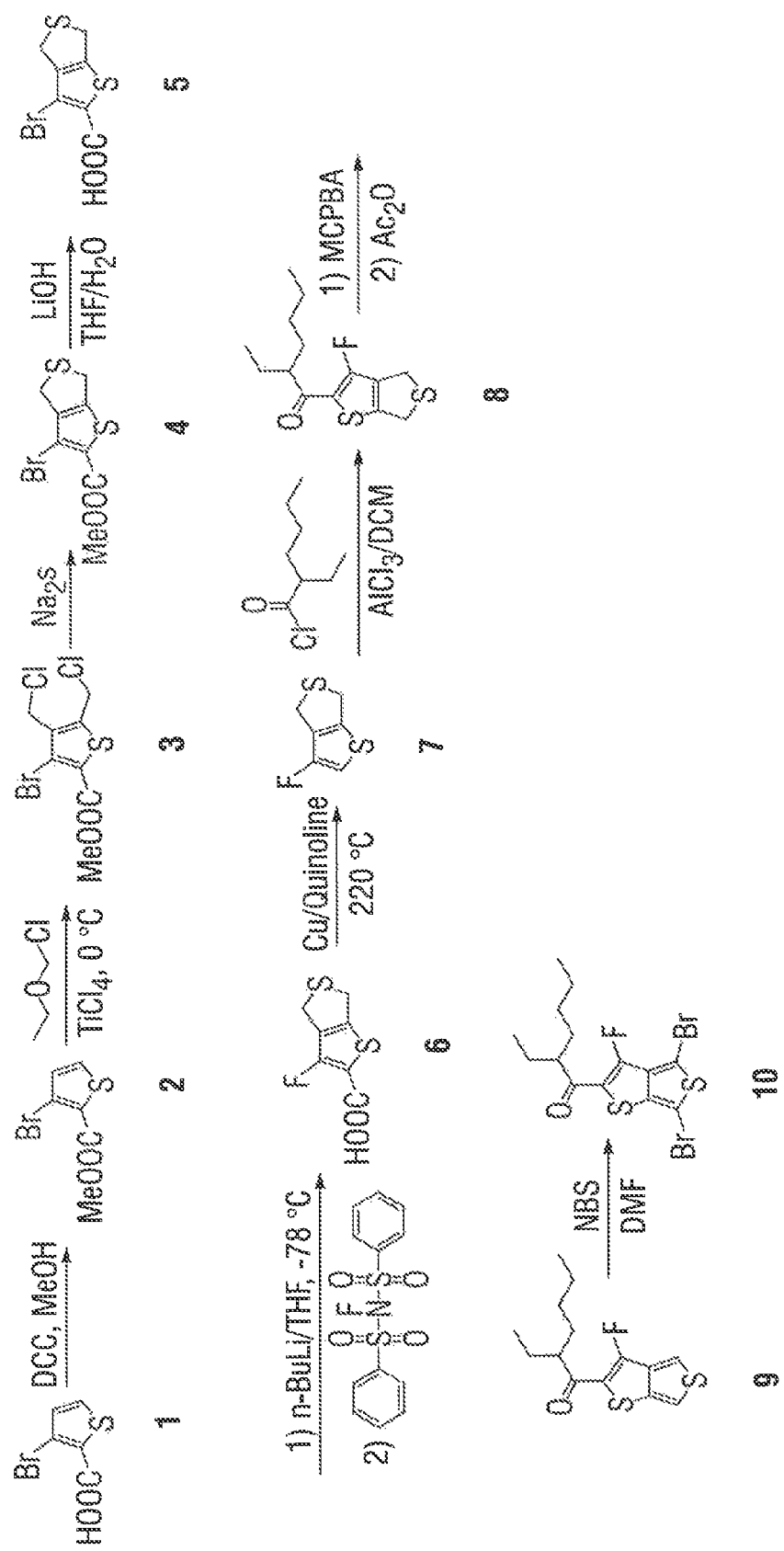
FIG. 2 shows the synthesis route of FTT-K according to an embodiment of the present invention.

The synthesis route to prepare 1-(4,6-dibromo-3-fluorothieno[3,4-b]thiophen-2-yl)-2-ethylhexan-1-one (FTT-K) is outlined in FIG. 2. As a general matter, using 3-bromothiophene-2-carboxylic acid or a protected derivative thereof as the starting material is crucial to this synthetic route. This ensures the later bromo-to-fluoro conversion at a significant improved rate, from less than about 20% to about 60-80%.

Synthesis of methyl 3-bromothiophene-2-carboxylate (2)

The starting material 3-bromothiophene-2-carboxylic acid is commercially available, e.g., from Sigma Aldrich, and can be purchased or made from simpler starting materials. It may also be possible to purchase protected derivatives of this chemical.

The 3-bromothiophene-2-carboxylic acid was first protected at the carboxylic group. 3-bromothiophene-2-carboxylic acid was dissolved in methanol containing catalytic DCC. Mixture was reacted by refluxing overnight. After solvent was evaporated, the residues were applied on silica gel. Methyl 3-bromothiophene-2-carboxylate was obtained as a colorless liquid.

Synthesis of methyl 3-bromo-4,5-bis(chloromethyl) thiophene-2-carboxylate (3)

1.873 mmol of methyl 3-bromothiophene-2-carboxylate (i.e., compound (2)) and 9.36 mmol of chloromethyl methyl ether were mixed in a 100 ml flask cooled by an ice bath, and then 2.8 mmol of titanium tetrachloride was added drop-wise over about 30 minutes. After removal of the ice bath, the reactants were stirred at about ambient temperature for one hour, and subsequently heated to about 50-60° C. and stirred for about six hours. The resulting sticky reactant was then poured into 100 g ice water and extracted by diethyl ether. After the removal of volatile solvent, methyl 3-bromo-4,5-bis (chloromethyl)thiophene-2-carboxylate was obtained as a dark brown oily product, which was used without any purification.

Synthesis of methyl 3-bromo-4,6-dihydrothieno[3,4-h]thiophene-2-carboxylate (4)

Compound (3) from the previous step was dissolved into 500 ml slightly boiling methanol, and a solution of sodium sulfide in 500 ml methanol was added drop-wise over about 1 hour at boiling temperature. The reactant was then kept at boiling temperature for about 1 hour. Methanol was removed by rotary evaporation and the sticky residue was absorbed by silica gel. The purification of product was performed by column chromatography using petroleum ether/ethyl acetate (30:1) as the eluent. Methyl 3-bromo-4,6-dihydrothieno[3,4-b]thiophene-2-carboxylate was obtained as colorless oil. The yield was about 75%.

Synthesis of 3-Bromo-4,6-dihydrothieno[3,4-h] thiophene-2-carboxylic acid (5)

Compound 4 from the previous step was dissolved in tetrahydrofuran (THF) and mixed with water containing LiOH. The reactants were stirred overnight. 3-Bromo-4,6-dihydrothieno[3,4-b]thiophene-2-carboxylic acid was obtained as a white crystal. The yield was about 75%.

Synthesis of 3-Fluoro-4,6-dihydrothieno[3,4-b] thiophene-2-carboxylic acid (6)

1.215 g of compound (5) (4.602 mmol) from the previous step was dissolved in THF. The mixture was cooled to about −78° C., and n-BuLi (2.5 M, 4.05 ml, 10.12 mmol) was added drop-wise to the mixture. The mixture was kept at about −78° C. for about 1 hour. N-fluoro-N-(phenylsulfonyl)benzenesulfonamide (2.17 g, 6.9 mmol) was then added. The resulting mixture was reacted at about −78° C. for about 2 hours, and then warmed up to about room temperature and reacted for about two hours. After reaction, the mixture was poured into water and extracted by ether. Compound 6 was obtained as a white solid. The yield was about 70%.

Synthesis of 3-fluoro-4,6-dihydrothieno[3,4-b]thiophene (7)

500 mg compound 6 from the previous step was mixed with 100 mg Cu powder and 20 ml quinolone. The mixture was

Synthesis of 2-ethyl-1-(3-fluoro-4,6-dihydrothieno [3,4-b]thiophen-2-yl)hexan-1-one (8)

2.31 mmol of $AlCl_3$ was added to 20 ml DCM with 2.31 mmol 2-ethylhexanoyl chloride at about 0° C. Compound 7 from the previous step was added to the mixture. The mixture was reacted at about 0° C. for about 4 hours. After reacting, the reactant was poured into ice water. The organic phase was extracted by ether 3 times. Compound 8 was purified by silica gel. The yield was about 70%.

Synthesis of 2-ethyl-1-(3-fluorothieno[3,4-h] thiophen-2-yl)hexan-1-one (9)

Compound 8 (233 mg, 0.812 mmol) from the previous step was dissolved into 20 ml chloroform and cooled down to about −40° C. by a liquid nitrogen/ethyl acetate bath, and then m-chloroperoxybenzoic acid (MCPBA) (140 mg, 0.812 mol) in chloroform (10 ml) was added drop-wise. After being stirred at about −40° C. for about 30 minutes, the reactant was warmed up to about ambient temperature and stirred for about 30 minutes. The chloroform was removed by rotary evaporation under vacuum, and 30 ml acetic acid anhydride was added to the reactant. The resulting mixture was refluxed for about 15 minutes. After removal of the volatile materials by rotary evaporation under vacuum, the oily residue was purified by column chromatography using petroleum ether/ethyl acetate (30:1) as eluent. Compound 9 (196.3 mg) was obtained. The yield was about 85%.

Synthesis of 1-(4,6-dibromo-3-fluorothieno[3,4-h] thiophen-2-yl)-2-ethylhexan-1-one (FTT-K) (10)

Compound 9 (196.3 mg, 0.69 mmol) from the previous step was dissolved in 10 ml DMF. Under the protection of an inert atmosphere, NBS (368.5 mg, 2.07 mmol) was added in one portion. The reactant was stirred for about 4 hours and then poured into 50 ml of 5% sodium thiosulfate solution with ice. The mixture was extracted by diethyl ether. The purification was conducted by column chromatography using petroleum ether as eluent. Compound 10 (173.6 mg) was obtained as a pale yellow oil. The yield was about 60%.

EXAMPLE 2

Synthesis of FTT-E

Figures 3, 4:
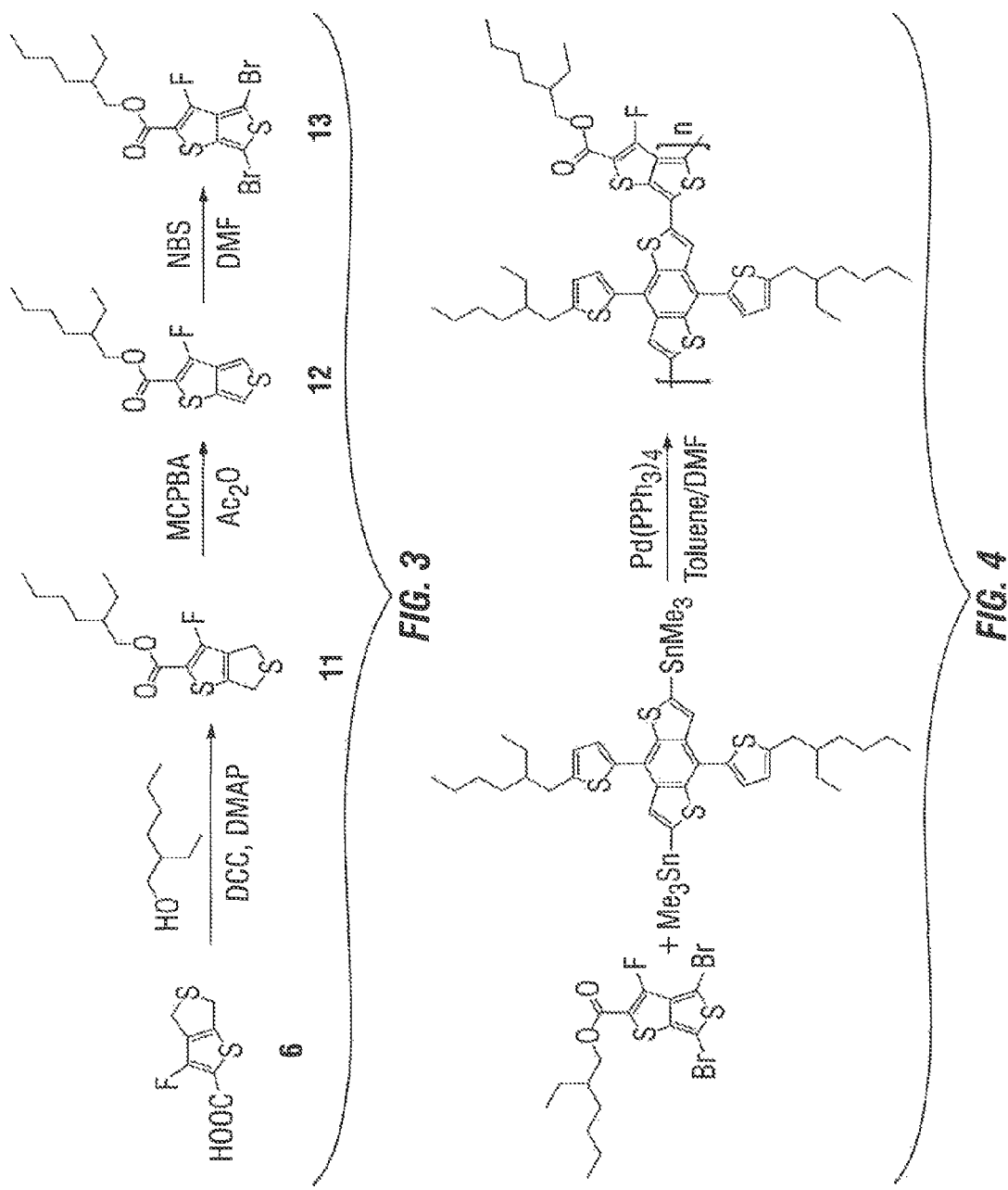
FIG. 3 shows the synthesis route of FTT-E according to an embodiment of the present invention.
FIG. 4 shows the synthesis route of CS-9 according to an embodiment of the present invention.

The synthetic route of FTT-E is illustrated in FIG. 3, wherein compound 6 from the previous example was used as the starting material.

Synthesis of 2-ethylhexyl 3-fluoro-4,6-dihydrothieno [3,4-h]thiophene-2-carboxylate (11)

500 mg of 3-fluoro-4,6-dihydrothieno[3,4-b]thiophene-2-carboxylic acid (2.45 mmol) was dissolved in 10 ml of dry methylene chloride. This solution was cooled to about 0° C. 530 mg of dicyclohexylcarbondiimide (DCC) (2.57 mmol), 30 mg of N,N-dimethylamino pyridine and 1 ml of 2-ethyl-hexan-1-ol was added. This reaction mixture was stirred at about 0° C. for about 1 hour and then warmed up to about room temperature for about 3 hours. The DCC salt was filtered off and the solution was poured into 50 ml water, and extracted with methylene chloride three times. The organic layer was dried over $Na_2SO_4$. After removal of the solvent by rotary evaporation, the residue was purified by column chromatography to yield 481 mg of product. The yield was about 62.1%.

Synthesis of 2-ethylhexyl 3-fluorothieno[2,3-c]thiophene-2-carboxylate (12)

475 mg of 2-ethylhexyl 3-fluoro-4,6-dihydrothieno[3,4-b] thiophene-2-carboxylate (1.50 mmol) was dissolved in 10 ml of ethyl acetate, the solution was cooled to −78° C. 337 mg of 77% m-CPBA (1.50 mmol) in 3 ml ethyl acetate was added and the reaction mixture was allowed to warm up to room temperature overnight. The solvent was removed by rotary evaporation and the residue was re-dissolved in 10 ml acetic anhydride, and heated to reflux for about 30 min. The solvent was removed by rotary evaporation and the product was purified by column (silica gel, hexane:dichloromethane=4:1) to produce 361 mg of product. The yield was about 76.5% for the two steps.

Synthesis of 2-ethylhexyl 4,6-dibromo-3-fluorothieno[3,4-h]thiophene-2-carboxylate (13)

350 mg of 2-ethylhexyl 3-fluorothieno[2,3-c]thiophene-2-carboxylate (1.11 mmol) was dissolved in 8 ml of dry DMF. This solution was cooled to about 0° C. 593 mg of NBS (3.33 mmol) in 3 ml DMF was added, and the reaction mixture was stirred at 0° C. for about 2 hours, then warmed up to about room temperature overnight. The reaction mixture was poured into 5% $Na_2S_2O_3$ aqueous solution and extracted with diethyl ether 3 times. The organic layer was dried over $Na_2SO_4$. After removal of solvent, the residue was purified by column to produce 265 mg of product. The yield was about 50.4%.

EXAMPLE 3

Synthesis of CS-9

(4,8-bis(5-(2-ethylhexyl)thiophen-2-yl)-benzo[1,2-b:4,5-b']dithiophene-2,6-diyl)bis(trimethylstannane) (0.271 g) and 2-ethylhexyl-3-fluorothieno[2,3-c]thiophene-2-carboxylate (0.141 g) from previous example were dissolved in 10 ml toluene with 2 ml DMF. The mixture was purged with argon for about 10 minutes, and then $Pd(PPh_3)_4$ (16 mg) was added. After being purged with argon for about 20 min, the reaction mixture was refluxed for about 16 hours under argon atmosphere. Then, the mixture was cooled to about room temperature, and the polymer was precipitated by addition of 100 ml methanol. The precipitated polymer was then re-dissolved in chloroform and again precipitated by hexane. The product was dried under vacuum to obtain 0.226 g of a dark blue solid. The yield was about 75%.

EXAMPLE 4

Synthesis of FTT-K by Conventional Method

Figure 6:
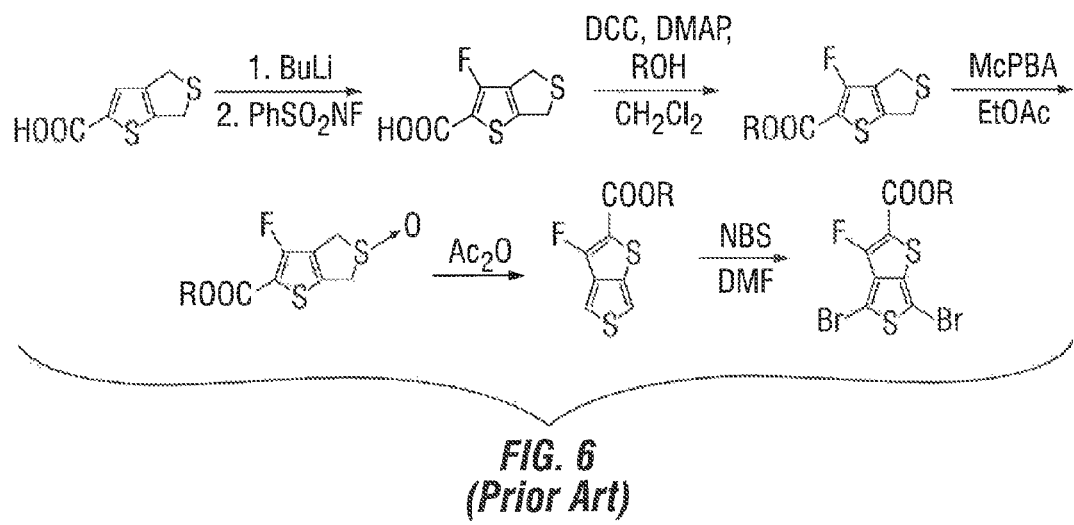
FIG. 6 shows the conventional synthesis route of FTT.

The fluorinated thieno[3,4-b]thiophene was synthesized via a modified route previously reported for ester substituted thieno[3,4-b]thiophene as shown in FIG. 6 and described in more detail in Liang, J. Am. Chem. Soc. 131 (2009b) pp. 7792-7799. The fluorine was introduced to the fused ring unit from 4,6-dihydrothieno[3,4-b]thiophene-2-carboxylic acid after deprotonation by using BuLi and reacting with PhSO$_2$NF. The fluorinated acid was first converted to an ester and then dibromo-substituted thieno[3,4-b]thiophene.

EXAMPLE 5A

Fabrication of Regular Photovoltaic Devices

The polymer from Example 3 was co-dissolved with PC$_{61}$BM in a mixed solvent in the weight ratio of 1:1.6, respectively. The concentrations were 10 mg/ml, and the mixed solvent was dichlorobenzene/1,8-diiodooctane (97/3, v/v).

Indium Tin Oxide (ITO)-coated glass substrates (15 Ω/sq) were cleaned stepwise in detergent, water, acetone and isopropyl alcohol under ultrasonication for about 15 minutes each and, subsequently, dried in an oven. A thin layer (~30 nm) of PEDOT:PSS (Baytron P VP Al 4083) was spin-coated onto ITO surface, which was pre-treated by ultraviolet ozone for about 15 min. Low conductivity PEDOT:PSS was chosen to minimize measurement error from device area due to lateral conductivity of PEDOT:PSS.

After being baked at about 150° C. for about 10 min, the substrates were transferred into a nitrogen filled glove box (<0.1 ppm O$_2$ & H$_2$O). A polymer/PC$_{61}$BM composite layer (ca. 100 nm thick) was then spin-cast from the blend solutions at 1000 rpm on the ITO/PEDOT:PSS substrate without further special treatments. Then the film was transferred into the thermal evaporator, which is located in the same glove box. A Calcium layer (25 nm) and an Aluminum layer (80 nm) were deposited in sequence under the vacuum of 2×10$^{-6}$-Torr. The effective area of film was measured to be 0.095 cm$^2$. An exemplary diagram is provided as FIG. 7a.

EXAMPLE 5B

Fabrication of Inverted Photovoltaic Devices

The polymer from Example 3 was co-dissolved with PC$_{61}$BM in a mixed solvent in the weight ratio of 1:1.6, respectively. The concentrations were 10 mg/ml, and the mixed solvent was dichlorobenzene/1,8-diiodooctane (97/3, v/v).

Indium Tin Oxide (ITO)-coated glass substrates (15 Ω/sq) were cleaned stepwise in detergent, water, acetone and isopropyl alcohol under ultrasonication for about 15 minutes each and, subsequently, dried in an oven. A thin layer (~10 nm) of Zinc acetate dihydrate was spin-coated onto ITO surface, which was pre-treated by ultraviolet ozone for 15 min.

After being baked at about 170° C. for about 15 min, the substrates were transferred into a nitrogen filled glove box (<0.1 ppm O$_2$ & H$_2$O). A polymer/PC$_{61}$BM composite layer (ca. 100 nm thick) was then spin-cast from the blend solutions at 1000 rpm on the ITO/PEDOT:PSS substrate without further special treatments. Then the film was transferred into the thermal evaporator, which is located in the same glove box. A MoO$_3$ layer (10 nm) and a silver layer (100 nm) were deposited in sequence under the vacuum of 2×10$^{-6}$-Torr. The effective area of film was measured to be 0.095 cm$^2$. An exemplary diagram is provided as FIG. 7b.

EXAMPLE 6

Current-Voltage Measurement

The fabricated device was encapsulated in a nitrogen filled glove box by UV epoxy (bought from Epoxy Technology) and cover glass. The current density-voltage (J-V) curves were measured using Keithley 2400 source-measure unit. The photocurrent was measured under AM 1.5 G illumination at 100 mW/cm$^2$ under Newport Thermal Oriel 91192 1000 W solar simulator (4"×4" beam size). The light intensity was determined by a mono-silicon detector (with KG-5 visible color filter) calibrated by National Renewable Energy Laboratory (NREL) to minimize spectral mismatch.

External Quantum Efficiencies (EQEs) were measured using Model QEX7 purchased from PV Measurements, Inc. A calibrated mono silicon diode with known spectral response was used as a reference.

EXAMPLE 6

Photovoltaic Properties Comparison

Figure 5:
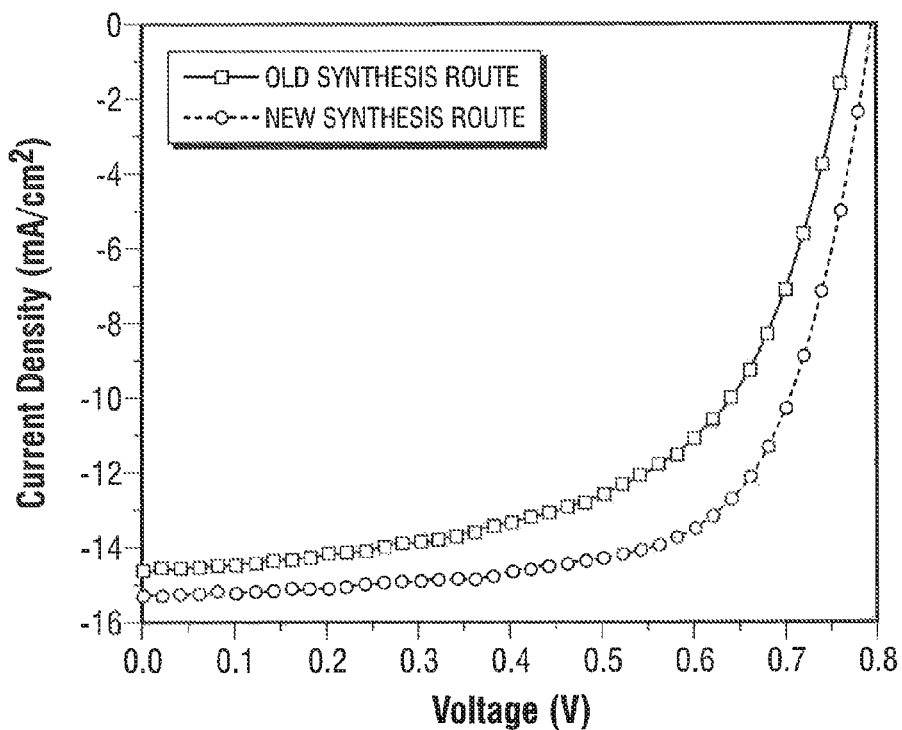
FIG. 5 shows the current density-voltage relationship of solar cells made of the polymers synthesized by the method of the present invention and by conventional method.

The comparison of Current Density-Voltage relationship of the two devices, one made of the polymer synthesized by the method of the present invention and the other by conventional method, is shown in FIG. 5.

As shown in FIG. 5, the device made with the polymer synthesized by the method of the present invention exhibits higher open circuit voltage than the polymer synthesized by conventional method. Specifically, the device fabricated by the polymer synthesized by the present invention has an open circuit voltage of 0.80 V, whereas the conventional synthesis route gives only 0.78 V. Additionally, as shown in the table below, the device fabricated by the polymer synthesized by the present invention also has higher short circuit current density (Jsc), Fill Factors (FF) and power conversion efficiency (PCE) comparing to the polymer synthesized by conventional method.

|  | Voc | Jsc (mA/cm$^2$) | FF (%) | PCE (%) |
|---|---|---|---|---|
| Conventional synthesis route | 0.78 | 14.7 | 58.6 | 6.71 |
| New synthesis route | 0.80 | 15.8 | 66.7 | 8.41 |

These results show that the synthetic method of the present invention not only achieves higher conversion rate in the synthesis, but also provides product of higher quality to be used in photovoltaic applications.

The embodiments and examples set forth herein are presented to best explain the present invention and its practical application and to thereby enable those skilled in the art to make and utilize the invention. However, those skilled in the art will recognize that the foregoing description and examples have been presented for the purpose of illustration and example only. The description as set forth is not intended to be exhaustive or to limit the invention to the precise form disclosed. Many modifications and variations are possible in light of the above teaching without departing from the spirit and scope of the following claims.

Definitions

As used herein, the terms "a," "an," "the," and "said" means one or more, unless the context dictates otherwise.

As used herein, the term "about" means the stated value plus or minus a margin of error or plus or minus 10% if no method of measurement is indicated.

As used herein, the term "or" means "and/or" unless explicitly indicated to refer to alternatives only or if the alternatives are mutually exclusive.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "containing," "contains," and "contain" have the same open-ended meaning as "comprising," "comprises," and "comprise," provided above.

As used herein, the terms "having," "has," and "have" have the same open-ended meaning as "comprising," "comprises," and "comprise," provided above.

As used herein, the terms "including," "includes," and "include" have the same open-ended meaning as "comprising," "comprises," and "comprise," provided above.

As used herein, the phrase "consisting of" is a closed transition term used to transition from a subject recited before the term to one or more material elements recited after the term, where the material element or elements listed after the transition term are the only material elements that make up the subject. However, non-material elements that do not substantially change the nature of the invention, such as various buffers, differing salts, extra wash or precipitation steps, pH modifiers, and the like, may be included in the subject.

As used herein, the phrase "protected derivative" means a chemical that is protected at reactive groups that are not to be reacted in the subsequent steps, such as the —COOH, e.g., by forming an ester at that group.

As used herein, the term "simultaneously" means occurring at the same time or about the same time, including concurrently.

As used herein, "starting material" means that the recited chemical is made or purchased for use as an early reactant in the synthetic pathway. However, if made, rather than purchased, there may be other ingredients that pre-date same.

Abbreviations

The following abbreviations are used herein:

| Abb. | Name | Structure |
|---|---|---|
| | 3-bromothiophene-2-carboxylic acid | |
| AC2O | Acetic anhydride, or ethanoic anhydride | 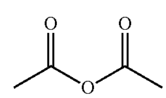 |
| BHJ | Bulk heterojunctions | |
| BDT | 4,8-dialkoxybenzo[1,2-b:4,5-b]dithiophene | 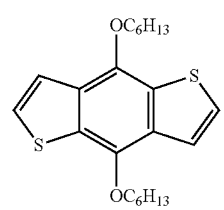 |
| BDT-FTT | benzo[1,2-b:4,5-b']dithiophene-fluorothienothiophene | 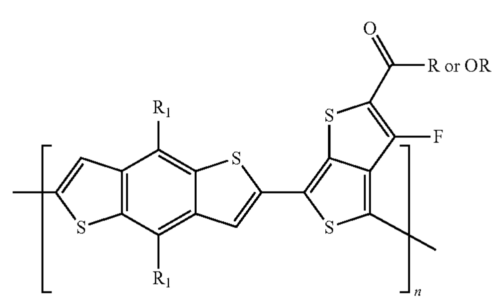 |

-continued

| Abb. | Name | Structure |
|---|---|---|
| CS-9 | P-2-ethylhexyl-4-(4,8-bis(5-(2-ethylhexyl)thiophen-2-yl)benzo[1,2-b:4,5-b']dithiophen-2-yl)-3-fluorothieno[3,4-b]thiophene-2-carboxylate | 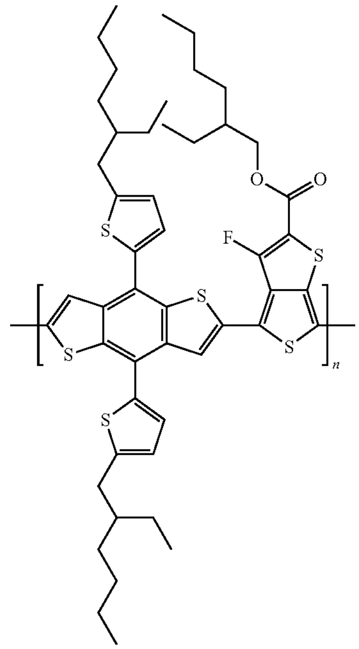 |
| DCC | N,N'-Dicyclohexylcarbodiimide | 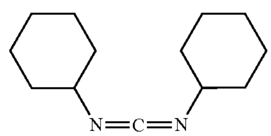 [SMILES: C(=NC1CCCCC1)=NC1CCCCC1] |
| DCM | Dichloromethane or methylene chloride | 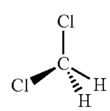 |
| DMAP | 4-Dimethylaminopyridine | 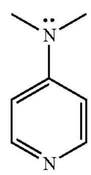 |
| DMF | Dimethylformamide | 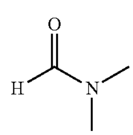 |
| FF | Fill Factor | |
| FTT | Fluorothieno[3,4-b]thiophene (usually a dibromo derivative herein) | |
| FTT-E | 2-alkyl-4,6-dibromo-3-fluorothieno[3,4-b]thiophene-2-carboxylate | 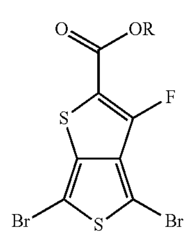 |

-continued

| Abb. | Name | Structure |
|---|---|---|
| FTT-K | 1-(4,6-dibromo-3-fluorothieno[3,4-b]thiophen-2-yl)-4-alkyl-1-one | 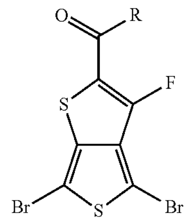 |
| FTT-K, alkyl is ethylhexan | 1-(4,6-dibromo-3-fluorothieno[3,4-b]thiophen-2-yl)-2-ethylhexan-1-one | 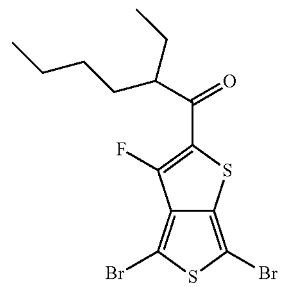 [SMILES: CCCCC(CC)C(=O)c1sc2c(Br)sc(Br)c2c1F] |
| HOMO | Highest occupied molecular orbital | |
| Jsc | Short Circuit Current Density | |
| LUMO | Lowest unoccupied molecular orbital | |
| MCPBA | m-chloroperoxybenzoic acid | 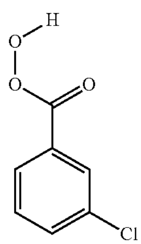 [SMILES: O=C(OO)c1cccc(Cl)c1] |
| MeOH | Methanol | |
| n-BuLi | n-Butyllithium | |
| NBS | N-Bromosuccinimide | 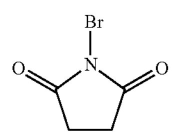 |
| OPV | organic photovoltaics | |
| OPVC | organic photovoltaic cell | |
| PCE | Power conversion efficiency | |
| $PC_{61}BM$ | [6,6]-phenyl-$C_{61}$-butyric acid methyl ester | 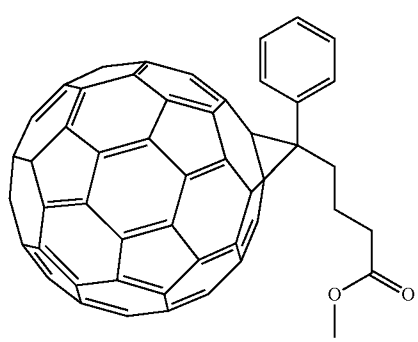 [SMILES: COC(=O)CCCC1(c2ccccc2)C2c3cc4c5c6c7c8c9c%10c%11c(cc%12cc%13cc%14c%15c%16c%13c(c%12%11)c9c%16c9c(c3c5c89)C%15C21C=%14)CC(C=C6C4)C7%10] |

-continued

| Abb. | Name | Structure |
|---|---|---|
| PC$_{71}$BM | [6,6]-phenyl-C$_{71}$-butyric acid methyl ester | 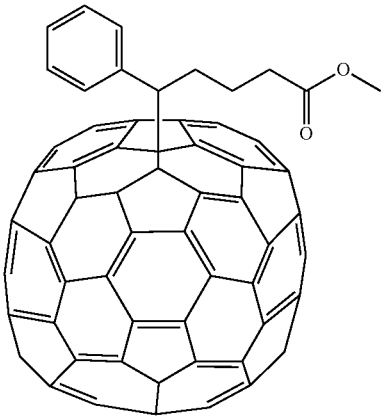 [SMILES: COC(=O)CCCC(c1ccccc1)C12c3c4ccc5c3-c3c6c7c8c9c%10c%11c(cc%12c%10c%10c%13c9c9c%14c%15c%16c(cc-5c3c%16c79)CC%15=CC(C=C%10C%12)C%13%14)-c3ccc-4c1c3C%11C8C62] |
| Pd(PPh$_3$)$_4$ | Tetrakis(triphenylphosphine) palladium | 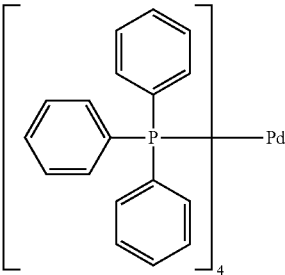 |
| PEDOT | Poly(3,4-ethylenedioxythiophene) | |
| PSS | poly(styrene sulfonate) | |
| PVC | photovoltaic cell, aka solar cell | |
| THF | Tetrahydrofuran | 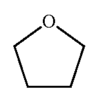 |
| TT | Thieno[3,4-b]thiophene (usually a dibromo derivative herein) | 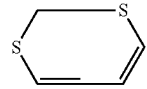 |
| TT-E | 2-alkyl-4,6-dibromothieno[3,4-b]thiophene-2-carboxylate | 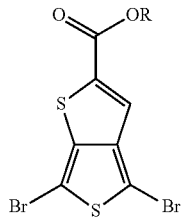 |
| TT-K | 1-(4,6-dibromothieno[3,4-b]thiophen-2-yl)-4-alkyl-1-one | 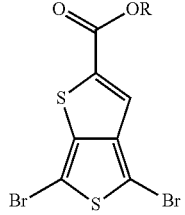 |
| VOC | Open Circuit Voltage | |

INCORPORATION BY REFERENCE

All patents and patent applications, articles, reports, and other documents cited herein are fully incorporated by reference to the extent they are not inconsistent with this invention. In particular, the following are incorporated by reference herein in their entirety:

WO03032072;
US20110124822;
WO2010008672;
US20110008926;
US20100276071;
US20100326497;
US20100018581;
US2010078074;
Hsiang-Yu Chen, et al., *Polymer Solar Cells with Enhanced Open-Circuit Voltage and Efficiency*, NATURE PHOTONICS 3 (2009) p. 649;
Lijun Huo, et al., *Replacing Alkoxy Groups with Alkylthienyl Groups: A Feasible Approach to Improve the Properties of Photovoltaic Polymers*, ANGELA. CHEM. INT. ED. 50(41) (2011) pp. 9697-9702;
Yongye Liang, et al., *For the Bright Future—Bulk Heterojunction Polymer Solar Cells with Power Conversion Efficiency of 7.4%*, ADV. ENERGY MATERIALS 22 (2010) pp. E135-E138;
Yongye Liang, *Development of New Semiconducting Polymers for High Performance Solar Cells*, J. AM. CHEM. SOC. 131 (2009a) pp. 56-57; and
Yongye Liang, *Highly Efficient Solar Cell Polymers Developed via Fine-Tuning of Structural and Electronic Properties*, J. AM. CHEM. SOC. 131 (2009b) pp. 7792-7799.

What is claimed is:

1. A method of making a fused heterocycle, comprising using a compound according to formula (I) or a protected derivative thereof as a starting material:

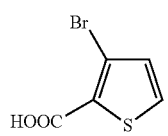
(I)

to form a fused heterocycle of formulae (II) or (III):

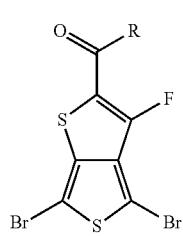
(II)

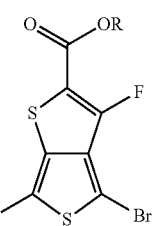
(III)

wherein R is hydrogen, $C_1$-$C_{20}$ alkyl, $C_1$-$C_{20}$ haloalkyl, aryl, heteroaryl, $C_1$-$C_{20}$ alkoxy, $C_1$-$C_{20}$ haloalkoxy, aryloxy, —$C_1$-$C_{20}$ alkyl-O—$C_1$-$C_{10}$ alkyl, —$C_1$-$C_{10}$ alkyl-O-aryl, nitro, halo, amino, or mono- or di alkyl amino.

2. The method of claim 1, wherein the method comprises the following reactions: i) protection of carboxylic acid with a protection group, ii) chloromethylation with two chloromethyl groups, iii) a cyclization reaction at the two chloromethyl groups, iv) hydrolysis of the carboxylate protection group, v) exchange fluorine for bromine, and vi) optional esterification of the carboxylate.

3. The method of claim 1, wherein the method comprises the following steps or their equivalents:

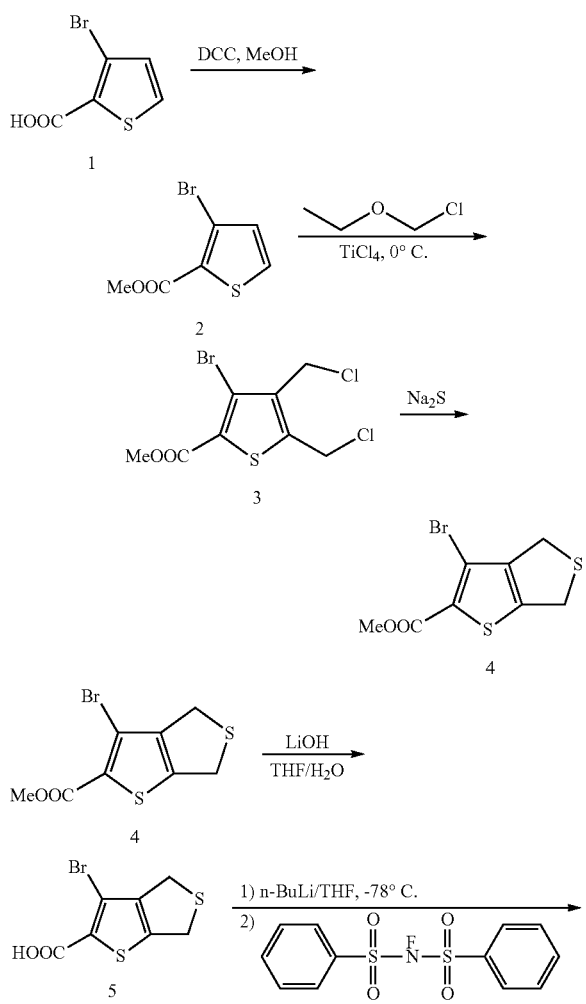

-continued
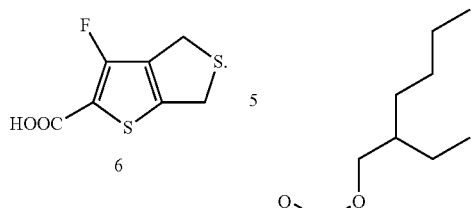
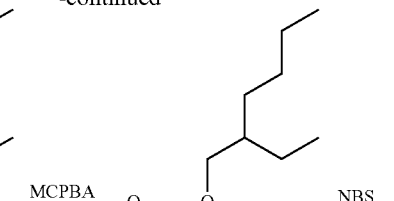
4. The method of claim 3, wherein the method comprises the following steps or their equivalents:
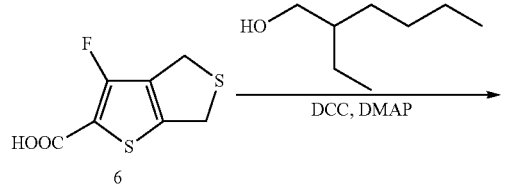
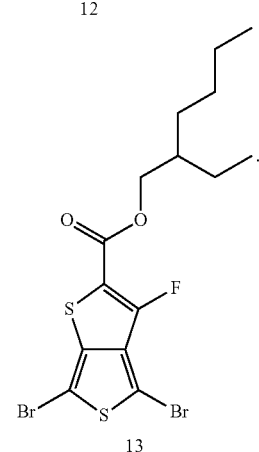
* * * * *

UNITED STATES PATENT AND TRADEMARK OFFICE
CERTIFICATE OF CORRECTION

PATENT NO. : 9,006,568 B2
APPLICATION NO. : 13/764919
DATED : April 14, 2015
INVENTOR(S) : Shuangxi Wang et al.

It is certified that error appears in the above-identified patent and that said Letters Patent is hereby corrected as shown below:

In the Specification

Column 10, lines 25 to 26, that portion of the term reading "[3,4-h]thiophene" should read --[3,4-b]thiophene--; line 39, that portion of the term reading "[3,4-h]thiophene" should read --[3,4-b]thiophene--

Column 11, line 17, that portion of the term reading "[3,4-h]thiophen-2-yl" should read --[3,4-b]thiophen-2-yl--; line 36, that portion of the term reading "[3,4-h]thiophen-2-yl" should read --[3,4-b]thiophen-2-yl--; line 58, that portion of the term reading "[3,4-h]thiophene" should read --[3,4-b]thiophene--

Column 12, line 25, that portion of the term reading "[3,4-h]thiophen-2-yl" should read --[3,4-b]thiophen-2-yl--; line 36, that portion of the term reading "[3,4-h]thiophene" should read --[3,4-b]thiophene--

Columns 19 and 20, structure for $PC_{61}BM$ [6,6]-phenyl-$C_{61}$butyric acid methyl ester reading " 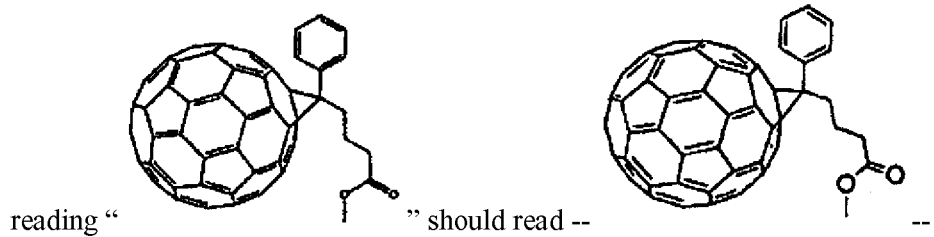 " should read -- --

Signed and Sealed this
Twenty-first Day of July, 2015

Michelle K. Lee
*Director of the United States Patent and Trademark Office*

CERTIFICATE OF CORRECTION (continued)

U.S. Pat. No. 9,006,568 B2

Columns 21 and 22, structure for PC$_{71}$BM [6,6]-phenyl-C$_{71}$-butyric acid methyl ester reading " " should read -- --

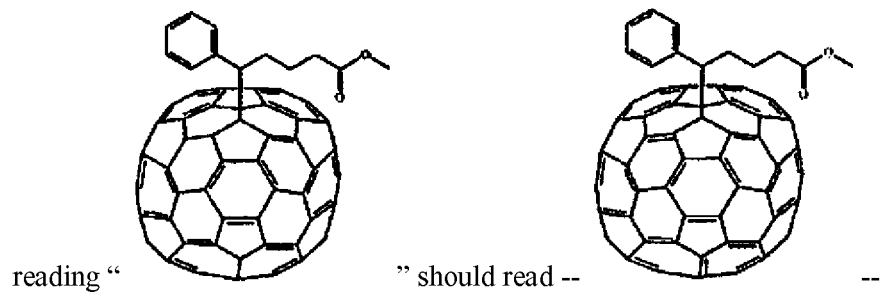

UNITED STATES PATENT AND TRADEMARK OFFICE
CERTIFICATE OF CORRECTION

PATENT NO. : 9,006,568 B2
APPLICATION NO. : 13/764919
DATED : April 14, 2015
INVENTOR(S) : Shuangxi Wang et al.

It is certified that error appears in the above-identified patent and that said Letters Patent is hereby corrected as shown below:

In the Specification

Columns 21 and 22, structure for TT Thieno[3,4-b]thiophene (usually a dibromo derivative herein)

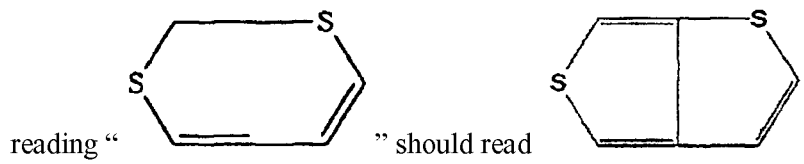

Signed and Sealed this
Eighth Day of September, 2015

Michelle K. Lee
*Director of the United States Patent and Trademark Office*